(12) United States Patent
DeVore et al.

(10) Patent No.: US 11,980,699 B2
(45) Date of Patent: May 14, 2024

(54) CARTILAGE REGENERATION USING INJECTABLE, IN SITU POLYMERIZABLE COLLAGEN COMPOSITIONS CONTAINING CHONDROCYTES OR STEM CELLS

(71) Applicant: Shanghai Qisheng Biological Preparation Co., Ltd., Shanghai (CN)

(72) Inventors: Dale P. DeVore, Chelmsford, MA (US); Jiaxun Zhu, Shanghai (CN)

(73) Assignee: Shanghai Qisheng Biological Preparation Co., Ltd., Shanghai (CN)

( * ) Notice: Subject to any disclaimer, the term of this patent is extended or adjusted under 35 U.S.C. 154(b) by 0 days.

(21) Appl. No.: 17/901,258

(22) Filed: Sep. 1, 2022

(65) Prior Publication Data

US 2023/0083186 A1    Mar. 16, 2023

Related U.S. Application Data

(60) Provisional application No. 63/239,496, filed on Sep. 1, 2021.

(51) Int. Cl.
*A61L 27/24* (2006.01)
*A61K 47/18* (2017.01)
*A61L 27/38* (2006.01)
*A61L 27/36* (2006.01)

(52) U.S. Cl.
CPC ........... *A61L 27/3852* (2013.01); *A61L 27/24* (2013.01); *A61L 27/3817* (2013.01); *A61L 27/3834* (2013.01); *A61L 27/3687* (2013.01); *A61L 2430/06* (2013.01)

(58) Field of Classification Search
CPC .. A61L 27/3852; A61L 27/24; A61L 27/3817; A61L 27/3834; A61L 27/3687; A61L 2430/06
See application file for complete search history.

(56) References Cited

U.S. PATENT DOCUMENTS

| 4,141,973 A | 2/1979 | Balazs |
| 4,164,559 A | 8/1979 | Dunn |
| 4,291,013 A | 9/1981 | Wahlig |
| 4,347,234 A | 8/1982 | Wahlig |

(Continued)

FOREIGN PATENT DOCUMENTS

| CN | 105879124 | 8/2016 |
| CN | 109224127 | 1/2019 |

(Continued)

OTHER PUBLICATIONS

Kontturi et al. (Drug Deliv and Transl Res. 2014;4:149-158). (Year: 2014).*

(Continued)

*Primary Examiner* — Ernst V Arnold
(74) *Attorney, Agent, or Firm* — Fitch, Even, Tabin & Flannery LLP

(57) ABSTRACT

The present disclosure describes a composition for cartilage defects or deficiencies repair, augmentation or treatment comprising an injectable, in situ polymerizable collagen composition and chondrocytes or stem cells in the collagen composition. The present disclosure also relates to methods for repairing or augmenting or treating cartilage defects or deficiencies using the composition and the preparation method of the composition.

21 Claims, 2 Drawing Sheets

(56) References Cited

U.S. PATENT DOCUMENTS

| | | |
|---|---|---|
| 4,424,208 A | 1/1984 | Wallace |
| 4,488,911 A | 12/1984 | Luck |
| 4,582,640 A | 4/1986 | Smestad |
| 4,582,865 A | 4/1986 | Balazs |
| 4,592,864 A | 6/1986 | Miyata |
| 4,605,691 A | 8/1986 | Balazs |
| 4,642,117 A | 2/1987 | Nguyen |
| 4,713,446 A | 12/1987 | Devore |
| 4,716,154 A | 12/1987 | Maelson |
| 4,716,224 A | 12/1987 | Sakurai |
| 4,784,990 A | 11/1988 | Nimrod |
| 4,803,075 A | 2/1989 | Wallace |
| 4,851,513 A | 7/1989 | Devore |
| 4,883,864 A | 11/1989 | Scholz |
| 4,937,270 A | 6/1990 | Hamilton |
| 4,963,666 A | 10/1990 | Maelson |
| 4,969,912 A | 11/1990 | Kelman |
| 4,992,226 A | 2/1991 | Piez |
| 5,017,229 A | 5/1991 | Burns |
| 5,067,961 A | 11/1991 | Kelman |
| 5,099,013 A | 3/1992 | Balazs |
| 5,103,840 A | 4/1992 | Kavoussi |
| 5,104,957 A | 4/1992 | Kelman |
| 5,162,430 A | 11/1992 | Rhee |
| 5,166,331 A | 11/1992 | della Valle |
| 5,201,764 A | 4/1993 | Kelman |
| 5,219,895 A | 6/1993 | Kelman |
| 5,292,802 A | 3/1994 | Rhee |
| 5,304,147 A | 4/1994 | Johnson |
| 5,306,500 A | 4/1994 | Rhee |
| 5,316,926 A | 5/1994 | Brown |
| 5,322,802 A | 6/1994 | Baliga |
| 5,324,519 A | 6/1994 | Dunn |
| 5,324,775 A | 6/1994 | Rhee |
| 5,328,955 A | 7/1994 | Rhee |
| 5,332,809 A | 7/1994 | Della Valle |
| 5,354,336 A | 10/1994 | Kelman |
| 5,356,883 A | 10/1994 | Kuo |
| 5,366,498 A | 11/1994 | Brannan |
| 5,376,375 A | 12/1994 | Rhee |
| 5,383,930 A | 1/1995 | Brannan |
| 5,411,874 A | 5/1995 | Ellwood |
| 5,413,791 A | 5/1995 | Rhee |
| 5,428,024 A | 6/1995 | Chu |
| 5,436,135 A | 7/1995 | Tayot |
| 5,446,091 A | 8/1995 | Rhee |
| 5,475,052 A | 12/1995 | Rhee |
| 5,476,515 A | 12/1995 | Kelman |
| 5,480,427 A | 1/1996 | Kelman |
| 5,492,135 A | 2/1996 | Devore |
| 5,502,081 A | 3/1996 | Kuo |
| 5,510,418 A | 4/1996 | Rhee |
| 5,527,893 A | 6/1996 | Burns |
| 5,550,188 A | 8/1996 | Rhee |
| 5,559,104 A | 9/1996 | Romeo |
| 5,565,519 A | 10/1996 | Rhee |
| 5,591,444 A | 1/1997 | Boss, Jr. |
| 5,631,243 A | 5/1997 | Kelman |
| 5,660,850 A | 8/1997 | Boss, Jr. |
| 5,665,372 A | 9/1997 | Boss, Jr. |
| 5,760,200 A | 6/1998 | Miller |
| 5,783,691 A | 7/1998 | Maelson |
| 5,800,541 A | 9/1998 | Rhee |
| 5,807,581 A | 9/1998 | Rosenblatt |
| 5,823,671 A | 10/1998 | Mitchell |
| 5,824,333 A | 10/1998 | Scopelianos |
| 5,830,708 A | 11/1998 | Naughton |
| 5,840,848 A | 11/1998 | Sturrock |
| 5,858,390 A | 1/1999 | Boss, Jr. |
| 5,861,486 A | 1/1999 | Devore |
| 5,874,500 A | 2/1999 | Rhee |
| 5,925,626 A | 7/1999 | della Valle |
| 6,013,679 A | 1/2000 | Kuo |
| 6,051,648 A | 4/2000 | Rhee |
| 6,071,530 A | 6/2000 | Polson |
| 6,129,761 A | 10/2000 | Hubbell |
| 6,150,461 A | 11/2000 | Takei |
| 6,161,544 A | 12/2000 | DeVore |
| 6,166,130 A | 12/2000 | Rhee |
| 6,284,284 B1 | 9/2001 | Naughton |
| 6,323,278 B2 | 11/2001 | Rhee |
| 6,337,389 B1 | 1/2002 | Wolfinbarger, Jr. |
| 6,458,889 B1 | 10/2002 | Trollsas |
| 6,511,958 B1 | 1/2003 | Atkinson |
| 6,521,244 B1 | 2/2003 | Kanesaka |
| 6,534,591 B2 | 3/2003 | Rhee |
| 6,682,760 B2 | 1/2004 | Noff |
| 6,833,408 B2 | 12/2004 | Sehl |
| 6,911,496 B2 | 6/2005 | Rhee |
| 6,916,910 B2 | 7/2005 | Wolfinbarger, Jr. |
| 7,025,916 B2 | 4/2006 | Bachrach |
| 7,064,187 B2 | 6/2006 | Stone |
| 7,157,428 B2 | 1/2007 | Kusanagi |
| 7,244,270 B2 | 7/2007 | Lesh |
| 7,314,636 B2 | 1/2008 | Caseres |
| 7,412,978 B1 | 8/2008 | Keller |
| 7,413,752 B2 | 8/2008 | Sawhney |
| 7,575,743 B2 | 8/2009 | Hunziker |
| 7,595,377 B2 | 9/2009 | Stone |
| 7,807,150 B2 | 10/2010 | Griffith |
| 7,883,693 B2 | 2/2011 | Sehl |
| 7,887,599 B2 | 2/2011 | Casares |
| 7,932,354 B2 | 4/2011 | Heimann |
| 8,067,031 B2 | 11/2011 | Daniloff |
| 8,084,055 B2 | 12/2011 | Voytik-Harbin |
| 8,124,120 B2 | 2/2012 | Sadozai |
| 8,455,459 B2 | 6/2013 | Wortzman |
| 8,580,289 B2 | 11/2013 | Seyedin |
| 8,607,044 B2 | 12/2013 | Hallam-Baker |
| 9,149,562 B2 | 10/2015 | Shortkroff |
| 9,480,775 B2 | 11/2016 | Guillen |
| 10,052,407 B2 | 8/2018 | Gleeson |
| 10,111,981 B2 | 10/2018 | Devore |
| 10,898,497 B2 | 1/2021 | Centeno |
| 11,235,089 B2 | 2/2022 | Devore |
| 2007/0065943 A1 | 3/2007 | Smith |
| 2008/0188416 A1 | 8/2008 | Bernstein |
| 2009/0012628 A1 | 1/2009 | Shortkroff |
| 2009/0117188 A1 | 5/2009 | Gershkovich |
| 2010/0172829 A1 | 7/2010 | Anderson |
| 2010/0210588 A1 | 8/2010 | Schwach-Abdellaoui |
| 2010/0217403 A1 | 8/2010 | Champion |
| 2011/0087152 A1 | 4/2011 | David |
| 2011/0301131 A1 | 12/2011 | Fitzpatrick |
| 2015/0367029 A1 | 12/2015 | Devore |
| 2020/0197568 A1 | 6/2020 | Lee |
| 2021/0138113 A1 | 5/2021 | Shoseyov |
| 2021/0161672 A1 | 6/2021 | Krom |
| 2022/0362437 A1 | 11/2022 | Devore |
| 2022/0362438 A1 | 11/2022 | Devore |
| 2023/0201418 A1 | 6/2023 | Devore |
| 2023/0203207 A1 | 6/2023 | Devore |

FOREIGN PATENT DOCUMENTS

| | | |
|---|---|---|
| CN | 109503864 | 3/2019 |
| CN | 109824919 | 5/2019 |
| CN | 110964215 | 4/2020 |
| CN | 111234271 | 6/2020 |
| WO | 1986000079 | 1/1986 |
| WO | 1986000912 | 2/1986 |
| WO | 1990009401 | 8/1990 |
| WO | 2012167226 | 12/2012 |

OTHER PUBLICATIONS

Rodriguez-Fontain et al. (Rev Asoc Argent Ortop Traumatol 2019;84(2):296-308). (Year: 2019).*

Sulaiman et al. (Polymers 2020;12:16 pages) (Year: 2020).*

Spiller et al. Tissue Engineering: Part B 2011;17(4):281-299) (Year: 2011).*

Kilmer et al. (ACS Biomater Sci Eng. Jun. 8, 2020; 6(6): 3464-3476) (Year: 2020).*

(56) References Cited

OTHER PUBLICATIONS

Duan, Wang-ping et. al., "Studies of Articular Cartilage Repair from 2009-2018: A Bibliometric Analysis of Articles." Orthopedic Surgery, vol. 13, 2021, pp. 608-615.

Musumeci, Giuseppe, et. al., "New perspectives for articular cartilage repair treatment through tissue engineering: A contemporary review." World Journal of Orthopedics, Apr. 2014, vol. 5, No. 2, pp. 80-88.

Stuart, Mary. "Cartilage Repair: What's the Right Combination?" Start-Up, vol. 14, No. 8, Sep. 2009, pp. 1-9.

Baumann, Leslie, et al. Chapter 23—"Dermal Fillers," in Cosmetic Dermatology—Principles and Practice. McGraw Hill, 2009, pp. 191-211.

Cockerham, Kimberly, et al., "Collagen-Based Dermal Fillers: Past, Present, Future," Facial Plastic Surgery, vol. 25, No. 2, 2009, pp. 106-113.

Denton, Andrew B. et al., Chapter 13—"Review of Collagen Fillers," in Office-based Cosmetic Procedures and Techniques. Cambridge University Press, 2010, pp. 59-64.

Lin, Yung-Kai, et al., "Studies of Novel Hyaluronic Acid-Collagen Sponge Materials Composed of Two Different Species of Type I Collagen," Journal of Biomaterials Applications, 2007, vol. 21, pp. 265-281.

Meyer, Karl, et al., "The polysaccharide of the vitreous humor." Journal of Biological Chemistry, 1934, 107, pp. 629-634.

Nobuhiko, Yui, et al., "Inflammation responsive degradation of crosslinked hyaluronic acid gels." Journal of Controlled Release, vol. 22, No. 2, 1992, pp. 105-116.

Nobuhiko, Yui, et al., "Regulated release of drug microspheres from inflammation responsive degradable matrices of crosslinked hyaluronic acid." Journal of Controlled Release, vol. 25, Nos. 1-2, 1993, pp. 133-143.

Reháková, Milena, et al., "Properties of collagen and hyaluronic acid composite materials and their modification by chemical crosslinking." Journal of Biomedical Materials Research, 1996, vol. 30, No. 3, pp. 369-372.

Tagle, Jorge M., et al., "Clinical Performance of a Dermal Filler Containing Natural Glycolic Acid and a Polylactic Acid Polymer," J. Aesthetic and Clinical Dermatology, vol. 3, No. 2, Feb. 5, 2010, pp. 42-47.

Cohen et al. "Artecoll: A Long-Lasting Injectable Wrinkle Filler Material: Report of a Controlled, Randomized, Multicenter Clinical Trial of 251 Subjects." Plastic and Reconstructive Surgery, 114(4), Sep. 15, 2004, pp. 964-976.

De Vore, Dale P., "Collagen as an Ophthalmic Biomaterial." In Encyclopedic Handbook of Biomaterials & Bioengineering, Part B, Applications, Marcel Dekker, Inc., New York, 1995, Ch. 45, pp. 1233-1260.

Friess, Wolfgang. "Collagen-biomaterial for drug delivery." European Journal of Pharmacokinetics and Biopharmaceuticals, 1998, vol. 45, pp. 113-136.

International Search Report and Written Opinion, International Patent Application No. PCT/CN2022/116469, Dec. 1, 2022, 13 pages.

Nunez, Kristen. "What is Sodium Hyaluronate and How Is It Used in Skin Care?" <https://www.healthline.com/health/beauty-skin-care/sodium-hyaluronate#vs-hyaluronic-acid>, Nov. 6, 2020, 12 pages.

Silver and Garg, Collagen: Characterization, Processing and Medical Applications, In Handbook of Biodegradable Polymers, Eds. Domb, Kost, and Wiseman, Harwood Academic Publishing, Australia, Ch. 17).

Song, Xi et al., "A Novel Human-Like Collagen Hydrogel Scaffold with Porous Structure and Sponge-like Properties." POLYMERS, Dec. 31, 2017, No. 12, vol. 19, Article No.: 638, pp. 1-17.

\* cited by examiner ic acid, polyvinyl; alcohol, collagen plus ceramics, collagen plus glycosaminoglycan plus calcium phosphate, denatured fibrinogen plus polyethylene glycol, and poly(lactide-co-glycolide) plus calcium sulfate.
CARTILAGE REGENERATION USING INJECTABLE, IN SITU POLYMERIZABLE COLLAGEN COMPOSITIONS CONTAINING CHONDROCYTES OR STEM CELLS

CROSS-REFERENCE TO RELATED APPLICATION

This application claims priority to U.S. Provisional Patent Application No. 63/239,496, filed Sep. 1, 2021. The contents of the foregoing application are incorporated herein by reference in its entirety.

FIELD OF INVENTION

The present invention describes methods for supplementing or regenerating cartilagenous tissues using injectable, in situ polymerizable collagen-based compositions with active cells to enhance tissue regeneration. The compositions are in the form of clear, transparent, injectable viscous solutions with cellular components that rapidly undergo gelation and polymerization when contacted by physiological fluids. Upon injection into tissues, the solutions with intact cells rapidly undergo gelation and polymerization to form fibrous collagen matrices to supplement or regenerate deficient tissues.

BACKGROUND

Collagen compositions have been utilized for more than 30 years to augment or smooth out soft tissue defects such as dermal wrinkles and dermal folds, to volumize furrows, or to correct dermal contour unevenness and laxity. In addition, collagen-based compositions with cellular additives have been used to repair damaged cartilage.

Since cartilage is primarily composed of collagen-based matrices, it makes sense to correct cartilage defects and deficiencies with Type II collagen-based compositions. The collagen compositions utilized for cartilage repair have been comprised of either reconstituted collagen fibrils prepared from solubilized Type I collagen extracted from animal hides, reconstituted collagen fibrils prepared from soluble recombinant human collagen or intact collagen fibrils or fibers processed from human skin. In all cases the collagen composition has been composed of collagen fibrils/fibers or crosslinked collagen fibrils/fibers. In addition, fibrillar collagen compositions have been supplemented with chondrocytes or stem cells. In most cases collagen-based compositions for cartilage repair have been formed into implantable films or sponges.

There are several references describing the application of collagen for treating cartilage defects. Several key references are attached to this application. In addition there are many issued and pending patents referencing collagen for soft tissue augmentation. A list of these patents/patent applications is also attached to this application. Stuart (Start-up September 2005) lists a number of articular cartilage repair compositions including chitosan, Polyethylene glycol and hyaluronic acid, polyvinyl; alcohol, collagen plus ceramics, collagen plus glycosaminoglycan plus calcium phosphate, denatured fibrinogen plus polyethylene glycol, and poly (lactide-co-glycolide) plus calcium sulfate.

Musumeci, et al (World Journal of Orthopedics, 2014) lists natural materials for cartilage repair including silk, collagen, gelatin, fibrinogen, hyaluronic acid, alginate and synthetic materials including polyethylene glycol (PEG), polyglycolic acid (PGA), polymethylmethacrylate (PMMA), and polylactic-co-glycolic acid (PLGA). The repair compositions may include autologous cells or mesenchymal stem cells.

The solid phase of cartilage, comprising 95% of the tissue by volume, is composed principally of collagen (10% to 20% of total weight) and, to a lesser amount, proteoglycans (4% to 7% of the total weight). These together make up the extracellular matrix of articular cartilage. The collagen is principally type II collagen; however, types V, VI, IX, X, XI, XII, and XIV are also found in cartilage, but still collectively less than the amount of type II collagen.

SUMMARY OF INVENTION

This invention relates to methods to repair damaged or deficient articular cartilage using an injectable, in situ polymerizing collagen containing chondrocytes or stem cells (such as autologous chondrocytes or stem cells). The composition consists of a clear, viscous, soluble collagen at neutral pH that upon interacting with tissue fluids, instantly forms a cohesive clear gel that rapidly undergoes fibril formation to form an opaque collagen matrix. Previous studies of the in situ polymerizing collagen have demonstrated rapid conversion of the clear, viscous collagen base into well organized collagen fiber units shown to retain volume for time periods beyond 6 months.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

DETAILED DESCRIPTION OF THE INVENTION

Figure 1:
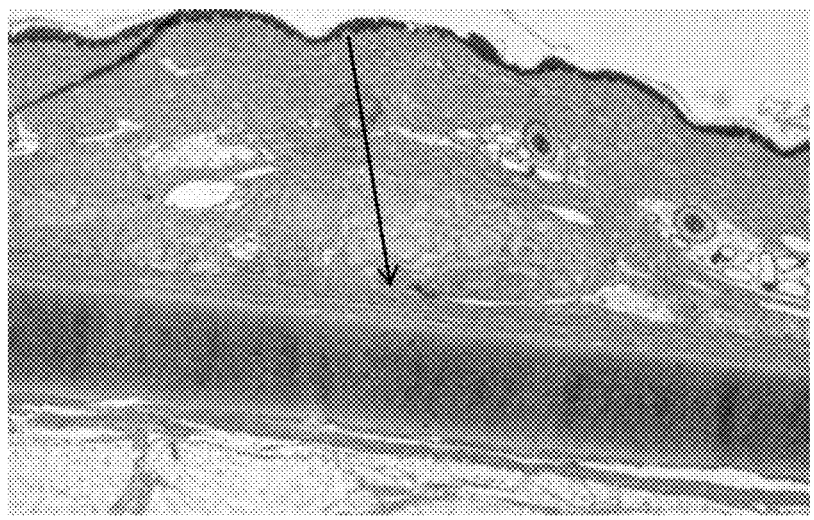
FIG. 1 is a histological image showing the cartilage augmentation effect of in situ polymerizing Type II collagen injected in pig ears for one month. Magnification 4×.

Described herein is a method for repairing damaged or deficient articular cartilage using an injectable, viscous, soluble collagen containing chondrocytes or stem cells (such as autologous chondrocytes or stem cells) capable of rapid polymerization when in contact with tissue fluids. The polymerizing collagen composition alone has previously been shown to augment soft tissues, such as correcting skin contour defects, or for enhancing soft tissue regeneration in animal models and in human clinical studies.

The base collagen used to prepare the in situ polymerizing collagen may be extracted and purified from animal articular cartilage or chicken sterna as described in U.S. Pat. No. 5,840,848 or purchased from Advanced Biomatrix. It is preferred that the base collagen be available in acid solution.

Previous Type I collagen compositions were initially soluble in form and, upon exposure to physiological fluids in vivo, rapidly polymerized to form intact collagen fibers. Previous Type I collagen solutions were prepared at concentrations ranging from 10 mg/ml to over 70 mg/ml and at pH's ranging from 6.0-8.0.

In one embodiment of the invention, a neutralized, acid soluble collagen (preferably Type II collagen), which remains in solution at physiological temperatures, is used to prepare in situ polymerizing collagen for cartilage tissue augmentation. These solutions must be extensively dialyzed against EDTA solutions and/or deionized water to reduce available cations and to prevent premature collagen fibrillogenesis. As the cations are removed, the pH of the collagen solution is increased to between about 6.8 and about 7.5 by adjusting the pH of the EDTA solution using 1 N sodium hydroxide. The collagen preparation does not undergo typical fibrillogenesis in the absence of added unbound or free cations.

In preferred embodiments, upon administration of the soluble collagen, the solution is converted to a gel or polymerized into a collagen fibrillar mass within 180 seconds, more preferably, within 120 seconds, most preferably, within 90 seconds. Preferably, the collagen-based solution is at a concentration of between 0.1-10%, more preferably, 0.5-7%, and most preferably between 2-5% collagen solids (w/v).

Autologous chondrocytes are extracted arthroscopically from a subject's healthy articular cartilage located on a non-load bearing area. The cells are expanded in cell culture to grow and expand the cells. Another option is to harvest and expand stem cells. In either case the expanded cells are added to the pure in situ polymerizing collagen composition for injection into the damaged or deficient articular cartilage.

Accordingly, it is an object of the invention to provide a method for using a neutralized, acid solubilized collagen solution containing autologous articular chondrocytes or stem cells suitable for use in treating or augmenting articular cartilage defects or deficiencies. When such compositions are injected into tissues, they quickly undergo gel formation and subsequent rapid fibrillogenesis when contacted with tissue fluids containing cationic constituents such as sodium chloride. RPC rapidly undergoes fibril formation even when injection into deionized (DI) water as some EDTA is diluted. Formation of collagen fibrils does not require interaction with physiological cationic constituents which leads to improved injectability and adhesion.

DEFINITIONS

By "collagen" is meant all forms of collagen including those which have been processed or modified, for example Type II collagen, preferably articular type II collagen. The collagen may be of human or animal origin or may be produced using recombinant techniques. The present invention can use these and other typed of collagen including natural collagen and various collagen derivatives.

By "tissue" is meant an aggregation of similarly specialized cells in an organism, preferably, mammalian, and, most preferably, human, where the cells are exposed to the organism's extracellular fluid, and are united in performance of a function within an organism. In particular, the present application refers to articular cartilage.

By "in situ polymerization" is meant rapid formation of a collagen gel and subsequently a collagen fibrous mass, upon injection of soluble collagen into tissue.

The present invention provides a number of advantages. For example, the collagen compositions described herein are biocompatible, biodegradable, and stable in solution at neutral pH. The ability to chemically manipulate the collagen to form a neutral stable solution allows for injectable administration through a fine gauge needle (e.g., a 30- or 31-gauge needle). In addition to the ease of application, injectable delivery of the collagen solution with autologous chondrocytes or stem cells allows access to the administration site while minimizing invasive injury to surrounding tissues. The density of the collagen solution is sufficient to fill an articular cartilage defect or other specific delivery site and remain in place until gelation and fibril formation occurs, and can correction of cartilage defects or deficiencies for at least 6 months.

SPECIFIC EMBODIMENTS

Further embodiments of the present invention are described again in the following. The present invention in particular also provides for the following items:

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

1. A composition for cartilage defect repair, augmentation or treatment comprising:
   (i) an injectable, in situ polymerizable collagen composition; and
   (ii) chondrocytes or stem cells comprised in part (i); and
   (iii) optionally, substance(s) for enhancing cartilage defect repair, augmentation or treatment and/or for enhancing cell proliferation and function; and/or
   (iv) optionally, a slowly resorbable scaffold or microcarriers.

2. The composition of item 1, wherein the source of collagen for part (i) is selected from allogeneic, mammal hides or marine species or axolotl hides derived matrix; and/or the collagen is selected from full collagen or atelocollagen, or recombinant collagen or recombinant collagen peptides from microorganism, plants, insect cells or animal cells, or collagen mimic peptides.

3. The composition of item 1, wherein the injectable, in situ polymerizable collagen composition comprises, a neutralized solution comprising the acid soluble collagen, EDTA or EGTA and a polyol, wherein the acid soluble collagen in the solution has not undergone fibrillogenesis prior to injection and is selected from the group consisting of Type I collagen, Type II collagen, Type III collagen and combinations of two or more types of collagen, preferably Type II collagen and combinations of Type II collagen with Type I and/or Type III collagen. In some embodiments, the rapidly polymerizing collagen gels are as described in U.S. Pat. No. 10,111,981B2.

4. The composition of item 3, wherein the acid soluble collagen in a concentration between 5 and 70 mg/ml; and/or
   wherein said EDTA/EGTA is disodium EDTA/EGTA; and/or
   wherein said EDTA/EGTA is in a concentration between 10 and 50 mM; and/or
   wherein said polyol is a sugar alcohol; and/or wherein said polyol is in a concentration between 2.5% and 4% (w/v); and/or wherein said rapidly polymerizing collagen gels further comprises a disaccharide, fructose, or combinations thereof; and/or wherein said rapidly polymerizing collagen gel has an osmolality of 260-360 mmol/kg.

5. The composition of item 1, wherein (A) the chondrocytes are one or more selected from group consisting of:
   autogenous or allogenous articular chondrocytes;
   autogenous or allogenous meniscal chondrocytes;
   autogenous or allogenous nasal septum chondrocytes;
   autogenous or allogenous auricular cartilage chondrocytes;
   chondrocytes differentiated from autogenous or allogenous progenitor cells and/or multipotent cells and/or pluripotent cells;
   engineered chondrocyte cell line, such as human chondrocyte cell line C20A4, C-28/I2, T/C-28a2, T/C-28a4, CHON-001; and
   xenogeneic chondrocytes; and/or (B) the stem cells are one or more selected from group consisting of:
   autogenous or allogenous progenitor cells including chondroprogenitors, chondroblasts;
   autogenous or allogenous multipotent cells including bone marrow-derived mesenchymal stems cells (BM-MSCs), placenta-derived mesenchymal stem cells (PMSCs); adipose tissue-derived mesenchymal stem cells (AD-MSCs); synovium-derived mesenchymal stems cells (Sy-MSCs); Umbilical cord blood-derived stem cells (UC-MSCs); Peripheral blood-derived mesenchymal stem cells (PB-MSCs); amniotic fluid stem cells (AFSCs); and
   autogenous or allogenous pluripotent cells including embryonic stem cells(ESCs); Induced pluripotent stem cells (iPSCs).

6. The composition of item 1, wherein the chondrocytes or stem cells are harvested from patient or appropriate donors or purchased from qualified tissue/cell banks; and/or
   the chondrocytes or stem cells are directly used after harvesting or cryopreservation and anabiosis; or are manipulated, modified, genetic-programmed and/or expanded in vitro before use; and/or
   the chondrocytes or stem cells are manipulated and sub-cultured/cultured for 1-30 weeks, preferably, 2-14 weeks; and/or
   the chondrocytes or stem cells are manipulated, modified, genetic-programmed and expanded in vitro and sub-cultures at passage 1, 2, 3, 4, 5, 6, 7, or 8, preferably passages 2-5.

7. The composition of item 1, wherein the amount of collagen in part (i) is from 0.1 wt % to 10 wt %, and the cell density of chondrocytes or stem cells in part (ii) is from $0.5 \times 10^5$ cells/mL to $2 \times 10^8$ cells/mL, preferably from $1 \times 10^6$ cells/mL to $5 \times 10^7$ cells/mL.

8. The composition of item 1, wherein part (ii) is added to part (i) by directly mixing cell-containing tissue extracts or cell culture media or matrices/scaffold with a sterile medical two-way or three-way syringe plug valve; and/or
   part (iii) is added to part (i) or part (ii) or a mixture of part (i) and part (ii) with a sterile medical two-way or three-way syringe plug valve; and/or
   part (iv) is combined with part (i), (ii), (iii) or any combinations thereof by:
      (a) culturing part (ii) on part (iv) and further adding combination of part (ii), part (iv) with or without part (iii) to part (i) with a sterile medical two-way or three-way syringe plug valve;
      (b) adding part (iv) to part (i) by utilizing vacuum planetary mixer to form an injectable homogeneous gel; and/or
      (c) adding part (iv) to a salt or salt or pH precipitate of part (i) and re-solubilized by dialysis or diafiltration or ultrafiltration process to form a homogeneous injectable gel.

9. The composition of item 1, wherein the substance(s) for enhancing cartilage defect repair, augmentation or treatment and/or for enhancing cell proliferation and function are selected from growth hormone, growth factors, cytokines, exosomes, other protein and/or proteoglycan and/or nutrition and trace elements.

10. The composition of item 9,
wherein the growth factors:
   (A1) are one or more selected from group consisting of: insulin-like growth factor including Insulin-like growth factor 1 (IGF-1) or Insulin-like growth factor-2(IGF-2); fibroblast growth factor family including fibroblast growth factor-2 (FGF-2); platelet-derived growth factors including platelet-derived growth factor-BB (PDGF-BB); epidermal growth factor (EGF) including EGF and HB-EGF; hepatocyte growth factor (HGF); stem cell factor(SCF); vascular endothelial growth factor (VEGF); bone morphogenetic proteins including BMP-1, BMP-2, BMP-3, BMP-4, BMP-5, BMP-6, BMP-7; colony-stimulating factors including macrophage colony-stimulating factor(M-CSF), granulocyte colony-stimulating factor (G-CSF), granulocyte macrophage colony-stimulating factor (GM-CSF); and/or
   (A2) are obtained from chemical synthesis, bio-extraction, genetic engineering and synthetic biology, or extracted from somatic/differentiated cells and/or stem cells; and/or
   (A3) are added into part (I) in a concentration of 5 to 100 ng/mL; and/or
   (A4) include: one or more of 50 ng/mL human epidermal growth factor, 50 ng/mL human fibroblast growth factor, 50 ng/mL human platelet-derived growth factor, or 50 ng/mL human insulin-like growth factor; and/or
wherein the growth hormones:
   (B1) are one or more selected from group consisting of: Insulin; Corticosteroid including hydrocortisone or dexamethasone; melatonin, and progesterone; and/or
   (B2) comprise insulin in a concentration of 5~100 mg/L; and/or
   (B3) comprise hydrocortisone in a concentration of 0.5~100 µg/L; and/or
   (B4) comprise dexamethasone in a concentration of 0.01~0.2 µg/L; and/or
   (B5) comprise progesterone in a concentration of 0.1~10 µg/L; and/or
   (B6) comprise melatonin in a concentration of 1 to 100 nM; and/or
wherein the cytokines:
   (C1) are one or more selected from group consisting of: Interleukin-1 family, Interleukin-2 family, Interleukin-6, transforming growth factors including transforming growth factor alpha and transforming growth factor beta 1 or 2 or 3 (TGF-β1 or TGF-β2 or TGF-β3); human monocyte chemoattractant protein-1 (MCP-1); intercellular cell adhesion molecules (ICAMs); tissue inhibitors of metalloproteinases (TIMPs) including TIMP1 and TIMP2; and/or
(C2) are obtained from chemical synthesis, bio-extraction, genetic engineering and synthetic biology, or extracted from somatic/differentiated cells and/or stem cells; and/or
(C3) are transforming growth factors in a concentration of 1 to 50 ng/mL; and/or wherein the exosomes:
(D1) are also known as Extracellular Vehicles (EVs), secreted by stem cells; and/or
(D2) have a size range from 100 nm to 500 nm or from 30 to 100 nm; and/or
(D3) are added in a concentration of 20 μg/mL-1000 μg/mL; and/or wherein proteins and/or proteoglycan:
(E1) are one or more selected from the group consisting of: fibronectin, laminin, decorin, decorin core protein, aggrecan and/or aggrecan monomer; biglycan; fibromodulin, lumican; epiphycan, perlecan; and/or
(E2) are added at a concentration of 10 μg/mL-1000 μg/mL, respectively; and/or wherein the nutrition:
(F1) are one or more selected from group consisting of: lipids including cholesterol, tocopherol acetate, arachidonic acid, cholesterol, Arachidonic acid, linoleic acid, linolenic acid, myristate acid, oleic acid, palmitic acid, palmitoleic acid and stearic acid; vitamins; and/or
(F2) comprise lipids added in an independent concentration of 50-1000 μg/L; and/or
(F3) comprise arachidonic acid in an independent concentration of 1~50 μg/L; and/or
(F4) comprise linoleic acid, linolenic acid, myristate acid, oleic acid, palmitic acid, palmitoleic acid, and/or stearic acid in an independent concentration of 10~200 μg/L; and/or
(F5) comprise vitamins selected from one or more of vitamin A, vitamin C, vitamin E, choline chloride, calcium pantothenate, folic acid, nicotinamide, pyridoxal hydrochloride, riboflavin, thiamine hydrochloride and inositol; and/or
(F6) comprise vitamins in an independent concentration of 0.1 to 2 mg/L; and/or
(F7) comprise ascorbic acid in an independent concentration of 0.5~100 mg/L; and/or
(F8) comprise amino acids and proteins selected from the group consisting of albumin, fetuin, fibronectin, putrescine, transferrin, serotonin, dopamine; and essential amino-acid including arginine, cystine, histidine, isoleucine, leucine, lysine, methionine, phenylalanine, threonine, tryptophan, tyrosine, valine; and non-essential amino acid including glutamine, glycine, alanine, asparagine, aspartic acid, glutamate, proline and serine; and/or
(F9) comprise proteins in an independent concentration of 0.1~20 g/L; and/or
(F10) comprise amino acids in an independent concentration of 0.01~20 mM; and/or wherein the trace elements:
(G1) are one or more selected from copper, zinc, selenium, iron, manganese, molybdenum, vanadium, nickel, tin, aluminum, silver, barium, bromine, cadmium, cobalt, chromium, fluorine, germanium, iodine, silicon, rubidium and zirconium; and/or
(G2) comprise copper, selenium, manganese, molybdenum, vanadium, nickel, tin, aluminum, silver, barium, bromine, cadmium, cobalt, chromium, fluorine, germanium, iodine, rubidium and/or zirconium in an independent concentration of 0.01~20 μg/L; and/or
(G3) comprise zinc, iron and/or silicon in an independent concentration of 100~1200 μg/L.

11.1 The composition of item 1, wherein the slowly resorbable scaffold or micro-carriers are one or more selected from the group consisting of:
reconstituted or crosslinked collagen fibrils/porous scaffold/micro-carrier;
reconstituted silk fibroin fibrils/porous scaffold/micro-carrier;
modified or crosslinked fibrin scaffold/micro-carrier;
Polymethylmethacrylate (PMMA) microspheres/porous scaffold/micro-carrier;
polymethylmethacrylate-hydroxyapatite microspheres/porous scaffold/micro-carrier;
crosslinked hyaluronic acid microspheres/porous scaffold/micro-carrier;
crosslinked or uncrosslinked gelation microspheres/porous scaffold/micro-carrier;
dextran microspheres/porous scaffold/micro-carrier;
polyethylene glycol (PEG) microspheres/porous scaffold/micro-carrier;
PEG-hydroxyapatite microspheres/porous scaffold/micro-carrier;
poly-L-lactide (PLA) microspheres/porous scaffold/micro-carrier;
PEG-PLA copolymer microspheres/porous scaffold/micro-carrier;
poly-L-lactide-hydroxyapatite microspheres/porous scaffold/micro-carrier;
polyglycolic acid (PGA) microspheres/porous scaffold/micro-carrier;
poly-L-lactide-hydroxyapatite microspheres/porous scaffold/micro-carrier;
polylactide and polyglycolide polymers and copolymers (PLGA) microspheres/porous scaffold/micro-carrier;
poly ε-caprolactone (PCL) microspheres/porous scaffold/micro-carrier;
PCL-PLA copolymer microspheres/porous scaffold/micro-carrier;
poly-ε-caprolactone-hydroxyapatite microspheres/porous scaffold/micro-carrier;
poly(p-dioxanone) (PDO) microspheres/porous scaffold/micro-carrier;
poly(p-dioxanone)-hydroxyapatite microspheres/porous scaffold/micro-carrier;
calcium hydroxyapatite microspheres/porous scaffold/micro-carrier; and
bioglass microspheres/porous scaffold/micro-carrier.

11.2. The composition of item 1 further comprising additive(s) selected from the group consisting of
local anesthesia drugs such as lidocaine, procaine, preferably in a concentration of from 0.1% to 0.5% by weight; and/or
a sulfur stabilizer or dissolution promotor, such as Chondroitin Sulfate Sodium (CS), Glucosamine Sulphate (GS) or Methyl sulfonyl methane (MSM), preferably in a concentration of from 0.1% to 5% by weight; and/or soluble small molecules added through dialysis process, diafiltration/ultrafiltration or tangential flow ultrafiltration with organic membranes or ceramic membrane with MWCO≥10 KDa.

12. A method for cartilage defect or deficiency repair, augmentation or treatment comprising administering a subject in need of such repair, augmentation or treatment with a composition of the present application, preferably the composition of any one of items 1~11. In some embodiments, the composition comprises:
   (i) an injectable, in situ polymerizable collagen composition; and
   (ii) chondrocytes or stem cells comprised in part (i); and
   (iii) optionally, substance(s) for enhancing cartilage defect repair, augmentation or treatment and/or enhancing cell proliferation and function; and/or
   (iv) optionally, a slowly resorbable scaffold or microcarriers.

13. The method of item 12, wherein the source of collagen for part (i) is selected from allogeneic, mammal hides or marine species or axolotl hides derived matrix; and/or the collagen is selected from full collagen or atelocollagen, or recombinant collagen or recombinant collagen peptides from microorganism, plants, insect cells or animal cells, or collagen mimic peptides.

14. The method of item 12, wherein the injectable, in situ polymerizable collagen composition comprises, a neutralized solution comprising the acid soluble collagen, EDTA or EGTA and a polyol, wherein the acid soluble collagen in the solution has not undergone fibrillogenesis prior to injection and is selected from the group consisting of Type I collagen, Type II collagen, Type III collagen and combinations of two or more types of collagen, preferably Type II collagen and the combination of Type II collagen with Type I and/or Type III collagen.

15. The method of item 14, wherein the acid soluble collagen in a concentration between 5 and 70 mg/ml; and/or
   wherein said EDTA/EGTA is disodium EDTA/EGTA; and/or
   wherein said EDTA/EGTA is in a concentration between 10 and 50 mM; and/or
   wherein said polyol is a sugar alcohol; and/or
   wherein said polyol is in a concentration between 2.5% and 4% (w/v); and/or
   wherein said rapidly polymerizing collagen gels further comprises a disaccharide, fructose, or combinations thereof; and/or
   wherein said rapidly polymerizing collagen gel has an osmolality of 260-360 mmol/kg.

16. The method of item 12, wherein the amount of collagen in part (i) is from 0.1 wt % to 10 wt %, and the cell density of chondrocytes or stem cells in part (ii) is from $0.5 \times 10^5$ cells/mL to $2 \times 10^8$ cells/mL.

17. The method of item 12, wherein the substance(s) for enhancing cartilage defect repair, augmentation or treatment and/or for enhancing cell proliferation and function are selected from growth hormone, growth factors, cytokines, exosomes, other protein and/or proteoglycan and/or nutrition and trace elements.

18. The method of item 12, wherein the composition is injected into articular cartilage; auricle, external auditory canal wall, eustachian tube and epiglottis, larynx; and/or intervertebral disc, articular disc and meniscus; and/or
   the cartilage is hyaline cartilage, elastic cartilage, fibrocartilage or any combinations thereof.

19. The method of item 12, wherein the composition is injected through an 18-~30-gauge needle or cannula, such as an 18-, 22-, 25-, 27- or 30-gauge needle or cannula.

20. The method of item 12, wherein upon administration, said injectable, in situ polymerizable collagen composition converts to a fibrous mass, adhering to cartilage within 180 seconds, or within 120 seconds, or further within 90 seconds.

21. A method for preparing a composition for cartilage defect repair, augmentation or treatment of the present application. In some embodiments, the method comprises combining parts (i)~(iv) to form the composition, wherein the composition comprises:
   (i) an injectable, in situ polymerizable collagen composition; and
   (ii) chondrocytes or stem cells comprised in part (i); and
   (iii) optionally, substance(s) for enhancing cartilage defect repair, augmentation or treatment and/or for enhancing cell proliferation and function; and/or
   (iv) optionally, a slowly resorbable scaffold or microcarriers;

22. The method of item 21, wherein the method comprises one or more of the steps selected from the group consisting of:
   adding part (ii) to part (i) by directly mixing cell-containing tissue extracts or cell culture media or matrices/scaffold with a sterile medical two-way or three-way syringe plug valve; and/or
   adding part (iii) to part (i) or part (ii) or a mixture of part (i) and part (ii) with a sterile medical two-way or three-way syringe plug valve; and/or
   combining part (iv) with part (i), (ii), (iii) or any combinations thereof by:
     (a) culturing part (ii) on part (iv) and further adding combination of part (ii), part (iv) with or without part (iii) to part (i) with a sterile medical two-way or three-way syringe plug valve;
     (b) adding part (iv) to part (i) by utilizing vacuum planetary mixer to form an injectable homogeneous gel; and/or
     (c) adding part (iv) to a salt or salt or pH precipitate of part (i) and re-solubilized by dialysis or diafiltration or ultrafiltration process to form a homogeneous injectable gel.

Publications cited herein and the materials for which they are cited are hereby specifically incorporated by reference in their entireties. All reagents, unless otherwise indicated, were obtained commercially. All parts and percentages are by weight unless stated otherwise. An average of results is presented unless otherwise stated. The abbreviations used herein are conventional, unless otherwise defined.

EXAMPLES

Example 1. Preparation of In Situ Polymerizing Collagen Solution

The in situ polymerizing collagen was prepared using methods described previously by DeVore, et. al. (U.S. Pat. No. 10,111,981; assigned to Shanghai Haohai Biological Technology Co., LTD) Pure soluble Type II collagen was purchased from Advanced BioMatrix, Inc. or prepared as described in U.S. Pat. No. 5,840,848 (A. G Oberg Sturrock and D. P. DeVore). Sodium chloride was added to the soluble, pepsin-digested collagen solution (3 mg/mL) to a concentration of 0.8M to precipitate collagen. The white, opaque precipitate was recovered by centrifugation for 30 minutes at 3500 RPM and concentrated to approximately 50 mg/mL by placement on filter paper. The concentrated collagen precipitate was placed in dialysis tubing with a MW cut-off of 100,000 and dialyzed against 0.1N HCl for 16-18 hours. The resulting clear, viscous, redissolved collagen concentrate was then dialyzed against 0.035M EDTA (ethylenediaminetetraacetic acid, disodium salt dihydrate, SigmaUltra ~99%). Dialysis was continued for 5 days with daily adjustment of pH from the starting pH of 4.5 to a final pH of 7.5. The final clear and viscous collagen concentrate was collected and centrifuged to remove air bubbles. The final clear, viscous collagen exhibited a pH of 7.4 and did not undergo fibril formation at room temperature. Collagen fibrillogenesis was not triggered by pH or temperature.

Figure 2:
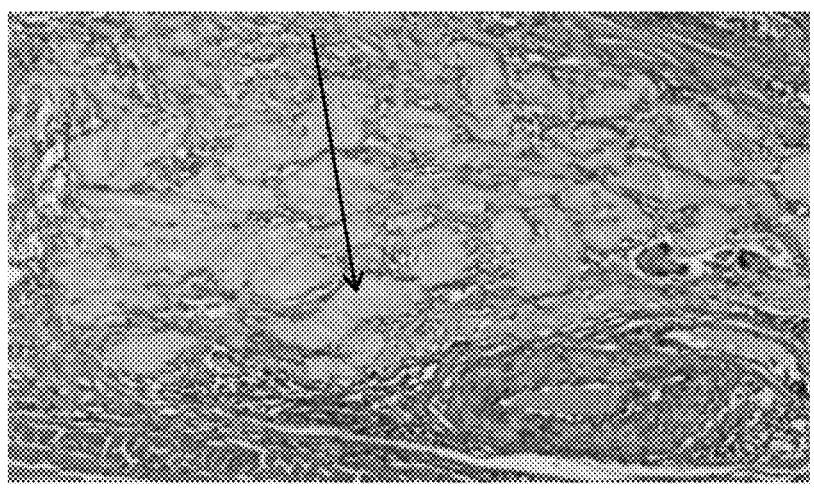
FIG. 2 is a histological image showing the cartilage augmentation effect of in situ polymerizing Type II collagen injected in pig ears for one month. Magnification 10×.

Evaluation of Gelation and Fibril Formation:

Aliquots of the in situ polymerizing collagen were injected into 0.8M sodium chloride at 37° C. and observed for the appearance of gel and fibrous collagen. The clear viscous collagen solution formed a white, opaque collagen matrix in less than 60 seconds. Aliquots of the in situ polymerizing collagen were also injected into deionized water at 37° C. and formed an opaque viscous mass within 3 minutes as EDTA was released from the collagen mass into the water. However, fibrils were not observed. In situ polymerizing collagen (RPC-II) was finally injected into ear in pig models for cartilage augmentation. (FIGS. 1 and 2) As shown by the one month histological images, the injected RPC-II effectively augmented cartilage tissues.

Expanding of Chondrocyte or Stem Cells:

The stem cells Cat.# ABC-FC0047 Human Adipose Derived Mesenchymal Stem Cell were expanded in a culture medium without animal serum nor any animal sourced composite. The cell culture medium is a DMEM contains 12 g/L sodium bicarbonate, 25 mM glutamate, 2 µg/L IL-1, 2.5 µg/L IL-2, 2 µg/L IL-3, 3 µg/L IL-6, 25 µg/L TNF-β1, 50 ng/mL EGF, 50 ng/mL FGF-2, 50 mg/mL insulin, 50 µg/L hydrocortisone, 5 µg/L progesterone, 5 mg/mL serotonin, 30 mg/L catechin, 50 nM melatonin, 50 mg/L transferrin, 10 g/L albumin, 8 g/L globulin, 50 µg/L fibronectin, 0.6 mM arginine, 0.1 mM cystine, 0.2 mM histidine, 0.4 mM isoleucine, 0.4 mM leucine, 0.4 mM lysine, 0.4 mM methionine, 0.2 mM phenylalanine, 0.4 mM threonine, 0.05 mM tryptophan, 0.2 mM tyrosine, 0.4 mM valine, 0.1 mM glycine, 0.1 mM alanine, 0.1 mM asparagine, 0.1 mM aspartic acid, 0.1 mM glutamic acid, 0.1 mM proline, 0.1 mM serine, 1 mg/L nicotinamide, 1 mg/L folic acid, 1 mg/L pantothenic calcium, 1 mg/L pyridoxal hydrochloride, 0.1 mg/L riboflavin,1 mg/L thiamine hydrochloride, 2 mg/L inositol, 25 µM mercaptoethanol, 25 µg/L arachidonate, 600 µg/L cholesterol, 250 µg/L tocopheryl acetate, 100 µg/L linoleic acid, 100 µg/L linolenic acid, 100 µg/L myristic acid, 100 µg/L oleic acid, 100 µg/L palmitic acid, 100 µg/L stearic acid, 500 mg/mL polyether, 25 mg/mL Tween-80, 1 µg/L $CuSO_4$, 500 µg/L $ZnSO_4$, 10 µg/L $Na_2SeO_3$, 1000 µg/L $FeCl_3$, 500 µg/L $Na_2SiO_3$, 0.1 $MnSO_4$, 0.7 µg/L $MoO_3 \cdot 2H_2O$, 0.5 µg/L $NH_4VO_3$, 0.1 µg/L $NiSO_4$, 0.1 µg/L $SnCl_2$, 0.7 µg/L $AlCl_3$, 0.1 µg/L $AgNO_3$, 10 µg/L $Ba(C_2H_3O_2)_2$, 0.1 µg/L KBr, 10 µg/L $CdCl_2$, 10 µg/L $CoCl_2$, 0.5 µg/L $CrCl_3$, 10 µg/L NaF, 0.7 µg/L $GeO_2$, 0.5 µg/L KI, 0.7 µg/L RbCl, and 10 µg/L $ZrOCl_2$.

To achieve rapid cell proliferation to aimed numbers/concentration, scaffolds or micro-carriers were used. 10 mg~20 mg 3D—TableTrix® from CytoNiche were added to 2 mL cells suspension with cell concentration of 1.0~5.0× $10^6$ cells/mL and mixed gently and incubated for 1-2 hours. Additional 30-80 mL cell culture medium was added for expanding incubation for 2-7 days. The final cell concentration reached 1.0~10.0×$10^8$ cells/mL for further formulation or manipulation.

Addition of Chondrocytes or Stem Cells:

Chondrocytes from bovine source (product code: Bovine-1021) are purchased from Cellero. And stem cells (Cat.#: ABC-H0034Y Human Mesenchymal Stem Cells from Umbilical Cord Arteries or Cat.# ABC-FC0047 Human Adipose Derived Mesenchymal Stem Cell or ABC-FC0044 Human Bone Marrow-Derived Mesenchymal Stem Cell) are purchased from Accegen BioTechnology. Chondrocytes or stem cells are added to the viscous Type II in situ polymerizing collagen to a final concentration of 0.5×$10^7$ cells/mL to 1×$10^8$ cell/mL through mixing cell culture media including cells with Type II collagen solution with sterile two-way syringe plug valve.

Figure 3:
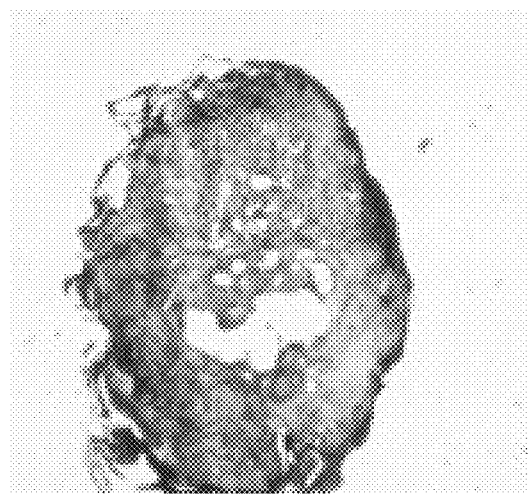
FIG. 3 is a histological image showing the chondrocyte and bone formation effect of in situ polymerizing Type II collagen containing MSCs implanted in nude mouse for 6 weeks. Magnification 4×.
Figure 4:
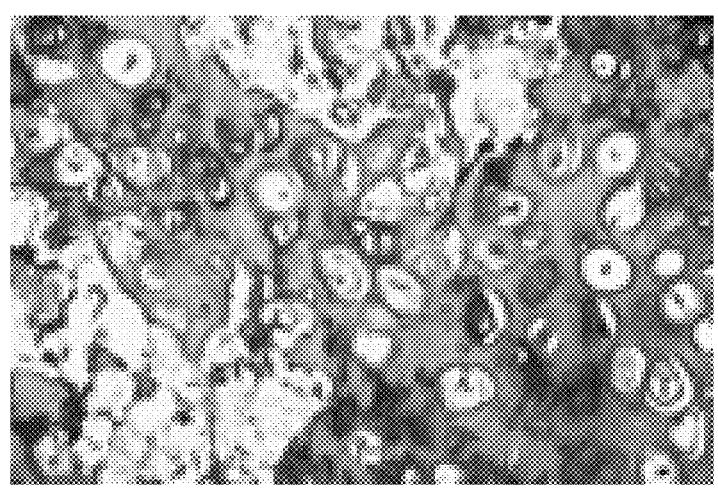
FIG. 4 is a histological image showing the chondrocyte and bone formation effect of in situ polymerizing Type II collagen containing MSCs implanted in nude mouse for 6 weeks. Magnification 40×. MSCs differentiated into chondrocytes and evidences of bone formation were observed.

In situ polymerizing collagen served as an injectable scaffold supporting cell proliferation and functions. Type II collagen provides a cartilage ECM-like environment induce stem cells differentiate into chondrocyte and produce contents including GAGs, polysaccharide, collagens of hyaline cartilage. Experiments showed good proliferation of MSCs in Type II in situ polymerizing collagen in vivo and the MSCs differentiated into chondrocyte and caused bone formation.(FIGS. 3 and 4)

Example 2. Evaluation of Injecting In Situ Polymerizing Collagen (RPC-II) in Animal Articular Cartilage Soluble, pepsin digested, Type II collagen is purchased from Advanced Biomatrix. In situ polymerizing collagen is prepared as described in Example 1 by extensive dialysis of salt precipitated collagen against 0.035M EDTA with stepwise increase in pH to 7.5. Collagen concentration is 37 mg/mL as assayed by hydroxyproline analysis. Chondrocytes (usually 0.5×$10^7$~5×$10^7$ cells) are added to the polymerizing collagen through mixing cell culture media including cells with Type II collagen solution with sterile two-way syringe plug valve and the composition is loaded into 27-gauge syringes.

All animal studies and evaluations are contracted to a facility, such as ArthroLab or a standard preclinical laboratory, such as Charles River Laboratories, with extensive experience in conducting studies for in vitro and in vivo studies to evaluate the efficacy of new compositions for treatment of osteoarthritis. In this study, fourteen purpose-bred female hound-mix dogs are utilized and divided into two groups The dogs undergo an arthroscopic procedure where two 6-8 mm-long full-thickness grooves in the medial femoral condylar cartilage using a 3 mm diameter ring curette. The justification of these grooves sizes is from an extensive literature search; and while there is not a standard groove size, the grooves chosen are commonly utilized sizes. Forty-eight hours post-surgery, the dogs in the treatment group are injected with Type II polymerizing collagen with chondrocytes (2~5 mL, depending on the size of the cartilage defect) into the articular cartilage defect. Dogs in the control group are untreated.

Sample Groups for the Study are Shown Below:

| Groups | Treatment | Evaluations |
| --- | --- | --- |
| Control<br>n = 6<br>Polymerizing<br>collagen with<br>chondrocytes<br>n = 6 | No treatment,<br>induced defect<br>Treatment,<br>induced defect | Gait upon walking and trotting will be evaluated;<br>Synovial fluid will be analyzed for proinflammatory biomarkers;<br>Macroscopic observation will allow measurement and scoring of<br>the gross morphological changes in the cartilage;<br>Biomechanical testing<br>Articular cartilage will be semi-quantitatively analyzed via<br>histology;<br>Gene expression analysis of cartilage tissue<br>The peripatellar synovium will be semi-quantitatively analyzed via<br>histology |

Characteristics Observed or Examined:

Clinical Evaluation included weight bearing on Lameness measure. At 4, 8, and 12 weeks after surgery, a clinical lameness assessment score are determined for all the canines.

Characterization Studies Post-Sacrifice:

After sacrifice, both operative and nonoperative knees are detached at the midfemur and midtibia and fixed in 10% neutral buffered formalin and prepared for histology. However, upon harvesting of the tissue, a portion of the articular cartilage is retained and snap-frozen for gene expression analysis. The peripatellar synovium from the operated knees is also fixed in 10% neutral buffered formalin. Sagittal sections of articular cartilage from the weight bearing areas of each femoral condyle and tibial plateau are dissected and sectioned as recommended by the OsteoArthritis Research Society International (OARSI). The samples are stained with H&E for general morphology and safranin-O for assessment of proteoglycan content. The following are measured:

1. Macroscopic Evaluations: A visual analogical scale (VAS) system is utilized to score the articular cartilage of the rabbit knee joints. The gross morphological changes in cartilage at the femoral condyles, tibial plateau, patella and trochlear groove is graded from 0 (no lesions) to 100 (exposure of subchondral bone). In addition, cartilage lesion sizes of the condyles and plateaus for the medial and lateral regions are also measured using a digital caliper. The amount of osteophytes at the articular surface is also graded from 0 to 3 with 0 being non-existent, 1—small/disputable, 2—evident, and 3—large.

2. Histologic analysis of cartilage and peripatellar synovium: Histopathology and histochemistry—Sagittal sections of articular cartilage from the weight bearing areas of each femoral condyle and tibial plateau are dissected as recommended by the OsteoArthritis Research Society International (OARSI). The samples are fixed in formalin, embedded, sectioned, and stained with H&E for general morphology and safranin-O for assessment of proteoglycan content. The histologic changes in the articular cartilage are evaluated using Mankin's histological and histochemical grading system (0-14). A minimum score of 0 is no cartilage degeneration and a maximum score of 14 is severe cartilage destruction. Additionally, the new cartilaginous tissue will be characterized. Biomarkers of native articular cartilage (type II collagen, aggrecan) and markers of fibroblastic or hypertrophic cartilage types, I and X collagen are identified using established immunohistochemical staining procedures (Mueller staining and imaging technique).

Additional parameters valuated include the following: erosion of cartilage, exposure of subchondral bone, fibrillation and/or fissures, loss of proteoglycan, disorganization of chondrocytes, loss of chondrocytes and cluster formation. The scoring system represents some of the most pertinent pathological changes in OA. The peripatellar synovium from the operated knees is also harvested and processed via histology. These samples will be stained with hematoxylin and eosin. Additional scoring will be performed on the severity of synovitis based on the range from 0-10.

Results from these studies show a significant improvement in joint function and reduction in erosion in joints treated with in situ polymerizing collagen with chondrocytes.

Although the present invention has been described with reference to exemplary embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention herein. Such equivalents are intended to be encompassed in the scope of the present invention.

All references, including patents, publications, and patent applications, mentioned in this specification are herein incorporated by reference in the same extent as if each independent publication, patent or patent application was specifically and individually indicated to be incorporated by reference.

REFERENCES

Relevant Technical Publications
1. Cartilage Repair: What's the Right Combination, Mary Stuart. Start-Up September 2005, 1-9
2. Studies of Articular Cartilage Repair from 2009-2018, A Bibliometric Analysis of Articles, Duan, Wang-ping et. al., Orthopedic Surgery 13:608-615, 2021
3. New perspectives for articular cartilage repair treatment through tissue engineering: A contemporary Review. Musumeci, G, et.al. World Journal of Orthopedics, April, 2014. Review of 59 published articles.

Patents Referencing Biomaterials for Cartilage Repair
1. U.S. Pat. No. 9,149,562: Ocugen—Method for use of a double-structured tissue implant for treatment of tissue defects
2. WO 2019/241099: Histogenics—Scaffold with adhesive for articular cartilage repair
3. US 2020/0197568: Preparation method and usage method for cartilage tissue recovery collagen 4. U.S. Pat. No. 7,157,428: Method for treatment and repair of meniscal injuries
5. U.S. Pat. No. 10,898,497: REGENEXX, LLC. Compositions and methods for cartilage repair
6. U.S. Pat. No. 10,052,407: Layered collagen and ha scaffold suitable for osteochondral repair
7. U.S. Pat. No. 7,575,743: Orthogene-Compositions and methods for the treatment and repair of defects or lesions in articular cartilage using synovial-derived tissue or cells
8. U.S. Pat. No. 16,973,987: Histogenics—Scaffold with adhesive for articular cartilage repair
9. U.S. Pat. No. 6,511,958: Zimmer Orthobiologics Inc.— Compositions for regeneration and repair of cartilage lesions
10. U.S. Pat. No. 10,111,981: Injectable in situ polymerizable collagen composition
11. U.S. Pat. No. 5,840,848: Method for preparation of type II collagen

The invention claimed is:

1. An in situ polymerizable collagen-based injectable composition for cartilage defect repair or treatment by injection comprising:
   (i) an injectable, in situ polymerizable collagen composition comprising: a neutralized solution comprising acid soluble collagen, EDTA or EGTA and a polyol, wherein the acid soluble collagen in the solution has not undergone fibrillogenesis prior to injection and is selected from one or more of Type I collagen, Type II collagen, and Type III collagen, wherein said acid soluble collagen is in a concentration of 5 to 70 mg/ml; and
   (ii) chondrocytes or stem cells comprised in part (i), wherein the in situ polymerizable collagen composition serves as an injectable scaffold supporting cell proliferation; and
   (iii) optionally, substance(s) for enhancing cartilage defect repair or treatment and/or for enhancing cell proliferation and function; and/or
   (iv) optionally, a slowly resorbable scaffold or microcarriers,
   wherein the in situ polymerizable collagen-based injectable composition with cellular components is in a form that rapidly undergo gelation and polymerization when contacted by physiological fluids and serves as a scaffold supporting cell proliferation.

2. The composition of claim 1, wherein the source of collagen for part (i) is selected from allogeneic, mammal hides or marine species or axolotl hides derived matrix; and/or the collagen is selected from full collagen or atelocollagen, or recombinant collagen or recombinant collagen peptides from microorganism, plants, insect cells or animal cells, or collagen mimic peptides.

3. The composition of claim 1,
   wherein said EDTA/EGTA is disodium EDTA/EGTA; and/or
   wherein said EDTA/EGTA is in a concentration between 10 and 50 mM; and/or
   wherein said polyol is a sugar alcohol; and/or
   wherein said polyol is in a concentration between 2.5% and 4% (w/v); and/or
   wherein said injectable, in situ polymerizable collagen composition further comprises a disaccharide, fructose, or combinations thereof; and/or
   wherein said injectable, in situ polymerizable collagen composition has an osmolality of 260-360 mmol/kg.

4. The composition of claim 1, wherein
   (A) the chondrocytes are one or more selected from group consisting of:
      autogenous or allogenous articular chondrocytes;
      autogenous or allogenous meniscal chondrocytes;
      autogenous or allogenous nasal septum chondrocytes;
      autogenous or allogenous auricular cartilage chondrocytes;
      chondrocytes differentiated from autogenous or allogenous progenitor cells and/or multipotent cells and/or pluripotent cells;
      engineered chondrocyte cell line; and
      xenogeneic chondrocytes; and/or
   (B) the stem cells are one or more selected from group consisting of:
      autogenous or allogenous progenitor cells including chondroprogenitors, chondroblasts;
      autogenous or allogenous multipotent cells including bone marrow-derived mesenchymal stems cells (BM-MSCs), placenta-derived mesenchymal stem cells (PMSCs); adipose tissue-derived mesenchymal stem cells (AD-MSCs); Synovium-derived mesenchymal stems cells (Sy-MSCs); Umbilical cord blood-derived stem cells (UC-MSCs); Peripheral blood-derived mesenchymal stem cells (PB-MSCs); amniotic fluid stem cells (AFSCs); and
   autogenous or allogenous pluripotent cells including embryonic stem cells (ESCs);
   Induced pluripotent stem cells (iPSCs).

5. The composition of claim 1, wherein the chondrocytes or stem cells are harvested from patient or appropriate donors or purchased from qualified tissue/cell banks; and/or
   the chondrocytes or stem cells are directly used after harvesting or cryopreservation and anabiosis; or are manipulated, modified, genetic-programmed and/or expanded in vitro before use; and/or
   the chondrocytes or stem cells are manipulated and sub-cultured/ cultured for 1-30 weeks; and/or
   the chondrocytes or stem cells are manipulated, modified, genetic-programmed and expanded in vitro and sub-cultures at passage 1, 2, 3, 4, 5, 6, 7, or 8.

6. The composition of claim 1, wherein the amount of collagen in part (i) is from 0.1 wt % to 10 wt %, and the cell density of chondrocytes or stem cells in part (ii) is from $0.5 \times 10^5$ cells/mL to $2 \times 10^8$ cells/mL.

7. The composition of claim 4, wherein the engineered chondrocyte cell line is one or more of human chondrocyte cell line C20A4, C-28/I2, T/C-28a2, T/C-28a4, CHON-001.

8. The composition of claim 1, wherein the substance(s) for enhancing cartilage defect repair or treatment and/or for enhancing cell proliferation and function are selected from growth hormone, growth factors, cytokines, exosomes, and/or nutrition and trace elements.

9. The composition of claim 8, wherein the growth factors:
   (A1) are one or more selected from group consisting of: insulin-like growth factor including Insulin-like growth factor 1 (IGF-1) or Insulin-like growth factor-2 (IGF-2); fibroblast growth factor family; platelet-derived growth factors; epidermal growth factor; hepatocyte growth factor (HGF); stem cell factor (SCF); vascular endothelial growth factor (VEGF); bone morphogenetic proteins; and colony-stimulating factors; and/or
   (A2) are obtained from chemical synthesis, bio-extraction, genetic engineering and synthetic biology, or extracted from somatic/differentiated cells and/or stem cells; and/or (A3) are added into part (I) in a concentration of 5 to 100 ng/mL; and/or
(A4) include: one or more of 50 ng/mL human epidermal growth factor, 50 ng/mL human fibroblast growth factor, 50 ng/mL human platelet-derived growth factor, or 50 ng/mL human insulin-like growth factor; and/or
wherein the growth hormones:
(B1) are one or more selected from group consisting of: Insulin; corticosteroid; melatonin, and progesterone; and/or
(B2) comprise insulin in a concentration of 5~100 mg/L; and/or
(B3) comprise hydrocortisone in a concentration of 0.5~100 μg/L; and/or
(B4) comprise dexamethasone in a concentration of 0.01~0.2 μg/L; and/or
(B5) comprise progesterone in a concentration of 0.1~10 μg/L; and/or
(B6) comprise melatonin in a concentration of 1 to 100 nM; and/or
wherein the cytokines:
(C1) are one or more selected from group consisting of: Interleukin-1 family, Interleukin-2 family, Interleukin-6, transforming growth factors; human monocyte chemoattractant protein-1 (MCP-1); intercellular cell adhesion molecules (ICAMs); tissue inhibitors of metalloproteinases (TIMPs); and/or
(C2) are obtained from chemical synthesis, bio-extraction, genetic engineering and synthetic biology, or extracted from somatic/differentiated cells and/or stem cells; and/or
(C3) are transforming growth factors in a concentration of 1 to 50 ng/mL; and/or
wherein the exosomes:
(D1) are secreted by stem cells; and/or
(D2) have a size range from 100 nm to 500 nm or from 30 to 100 nm; and/or
(D3) are added in a concentration of 20 μg/mL-1000 μg/mL; and/or
wherein the proteins and/or proteoglycan:
(E1) are one or more selected from the group consisting of: fibronectin, laminin, decorin, decorin core protein, aggrecan and/or aggrecan monomer; biglycan; fibromodulin, lumican; epiphycan, perlecan; and/or
(E2) are added at a concentration of 10 μg/mL~1000 μg/mL, respectively; and/or
wherein the nutrition:
(F1) are one or more selected from group consisting of: lipids including cholesterol, tocopherol acetate, arachidonic acid, cholesterol, Arachidonic acid, linoleic acid, linolenic acid, myristate acid, oleic acid, palmitic acid, palmitoleic acid and stearic acid; vitamins; and/or
(F2) comprise lipids added in an independent concentration of 50-1000 μg/L; and/or
(F3) comprise arachidonic acid in an independent concentration of 1~50 μg/L; and/or
(F4) comprise linoleic acid, linolenic acid, myristate acid, oleic acid, palmitic acid, palmitoleic acid, and/or stearic acid in an independent concentration of 10~200 μg/L; and/or
(F5) comprise vitamins selected from one or more of vitamin A, vitamin C, vitamin E, choline chloride, calcium pantothenate, folic acid, nicotinamide, pyridoxal hydrochloride, riboflavin, thiamine hydrochloride and inositol; and/or
(F6) comprise vitamins in an independent concentration of 0.1 to 2 mg/L; and/or
(F7) comprise ascorbic acid in an independent concentration of 0.5~100 mg/L; and/or
(F8) comprise amino acids and proteins selected from the group consisting of albumin, fetuin, fibronectin, putrescine, transferrin, serotonin, dopamine; and essential amino-acid including arginine, cystine, histidine, isoleucine, leucine, lysine, methionine, phenylalanine, threonine, tryptophan, tyrosine, valine; and non-essential amino acid including glutamine, glycine, alanine, asparagine, aspartic acid, glutamate, proline and serine; and/or
(F9) comprise proteins in an independent concentration of 0.1~20 g/L; and/or
(F10) comprise amino acids in an independent concentration of 0.01~20 nM; and/or wherein the trace elements:
(G1) are one or more selected from copper, zinc, selenium, iron, manganese, molybdenum, vanadium, nickel, tin, aluminum, silver, barium, bromine, cadmium, cobalt, chromium, fluorine, germanium, iodine, silicon, rubidium and zirconium; and/or
(G2) comprise copper, selenium, manganese, molybdenum, vanadium, nickel, tin, aluminum, silver, barium, bromine, cadmium, cobalt, chromium, fluorine, germanium, iodine, rubidium and/or zirconium in an independent concentration of 0.01~20 μg/L; and/or
(G3) comprise zinc, iron and/or silicon in an independent concentration of 100~1200 μg/ L.

10. The composition of claim 1, wherein the slowly resorbable scaffold or micro-carriers are one or more selected from the group consisting of:
reconstituted or crosslinked collagen fibrils/porous scaffold/micro-carrier;
reconstituted silk fibroin fibrils/porous scaffold/micro-carrier;
modified or crosslinked fibrin scaffold/micro-carrier;
Polymethylmethacrylate (PMMA) microspheres/porous scaffold/micro-carrier;
polymethylmethacrylate-hydroxyapatite microspheres/porous scaffold/micro-carrier;
crosslinked hyaluronic acid microspheres/porous scaffold/micro-carrier;
crosslinked or uncrosslinked gelatin microspheres/porous scaffold/micro-carrier;
dextran microspheres/porous scaffold/micro-carrier;
polyethylene glycol (PEG) microspheres/porous scaffold/micro-carrier;
PEG-hydroxyapatite microspheres/porous scaffold/micro-carrier;
poly-L-lactide (PLA) microspheres/porous scaffold/micro-carrier;
PEG-PLA copolymer microspheres/porous scaffold/micro-carrier;
poly-L-lactide- hydroxyapatite microspheres/porous scaffold/micro-carrier;
polyglycolic acid (PGA) microspheres/porous scaffold/micro-carrier;
poly-L-lactide-hydroxyapatite microspheres/porous scaffold/micro-carrier;
polylactide and polyglycolide polymers and copolymers (PLGA) microspheres/porous scaffold/micro-carrier;
poly ε-caprolactone (PCL) microspheres/porous scaffold/micro-carrier;
PCL-PLA copolymer microspheres/porous scaffold/micro-carrier;
poly-ε-caprolactone-hydroxyapatite microspheres/porous scaffold/micro-carrier;

poly(p-dioxanone)(PDO) microspheres/porous scaffold/micro-carrier;

poly(p-dioxanone)-hydroxyapatite microspheres/porous scaffold/micro-carrier;

calcium hydroxyapatite microspheres/porous scaffold/micro-carrier; and bioglass microspheres/porous scaffold/micro-carrier.

11. A method for cartilage defect or deficiency repair, augmentation or treatment comprising administering a subject in need of such repair, augmentation or treatment with a composition according to claim 1.

12. The method of claim 11, wherein the source of collagen for part (i) is selected from allogeneic, mammal hides or marine species or axolotl hides derived matrix; and/or the collagen is selected from full collagen or atelocollagen, or recombinant collagen or recombinant collagen peptides from microorganism, plants, insect cells or animal cells, or collagen mimic peptides.

13. The method of claim 11, wherein the injectable, in situ polymerizable collagen composition comprises, a neutralized solution comprising the acid soluble collagen, EDTA or EGTA and a polyol, wherein the acid soluble collagen in the solution has not undergone fibrillogenesis prior to injection and is selected from the group consisting of Type I collagen, Type II collagen, Type III collagen and combinations of two or more types of the collagen.

14. The method of claim 13, wherein the acid soluble collagen in a concentration between 5 and 70 mg/ml; and/or
wherein said EDTA/EGTA is disodium EDTA/EGTA; and/or
wherein said EDTA/EGTA is in a concentration between 10 and 50 mM; and/or
wherein said polyol is a sugar alcohol; and/or
wherein said polyol is in a concentration between 2.5% and 4% (w/v); and/or
wherein said rapidly polymerizing collagen gels further comprises a disaccharide, fructose, or combinations thereof; and/or
wherein said rapidly polymerizing collagen gel has an osmolality of 260-360 mmol/kg.

15. The method of claim 11, wherein the amount of collagen in part (i) is from 0.1 wt % to 10 wt %, and the cell density of chondrocytes or stem cells in part (ii) is from $0.5 \times 10^5$ cells/mL to $2 \times 10^8$ cells/mL.

16. The method of claim 11, wherein the substance(s) for enhancing cartilage defect repair, augmentation or treatment and/or for enhancing cell proliferation and function are selected from growth hormone, growth factors, cytokines, exosomes, other protein and/or proteoglycan and/or nutrition and trace elements.

17. The method of claim 11, wherein the composition is injected into articular cartilage; auricle, external auditory canal wall, eustachian tube and epiglottis, larynx; and/or intervertebral disc, articular disc and meniscus; and/or
the cartilage is hyaline cartilage, elastic cartilage, fibrocartilage or any combinations thereof.

18. The method of claim 11, wherein the composition is injected through an 18-~30-gauge needle or cannula.

19. The method of claim 11, wherein upon administration, said injectable, in situ polymerizable collagen composition converts to a fibrous mass, adhering to cartilage within 180 seconds, or within 120 seconds, or further within 90 seconds.

20. A method for preparing a composition for cartilage defect repair, augmentation or treatment comprising combining parts (i)~(iv) to form the composition according to claim 1.

21. The method of claim 20, wherein the method comprises one or more of the steps selected from the group consisting of:
adding part (ii) to part (i) by directly mixing cell-containing tissue extracts or cell culture media or matrices/scaffold with a sterile medical two-way or thee-way syringe plug valve; and/or
adding part (iii) to part (i) or part (ii) or a mixture of part (i) and part (ii) with a sterile medical two-way or thee-way syringe plug valve; and/or
combining part (iv) with part (i), (ii), (iii) or any combinations thereof by:
(a) culturing part (ii) on part (iv) and further adding combination of part (ii), part (iv) with or without part (iii) to part (i) with a sterile medical two-way or thee-way syringe plug valve;
(b) adding part (iv) to part (i) by utilizing vacuum planetary mixer to form an injectable homogeneous gel; and/or
(c) adding part (iv) to a salt or salt or pH precipitate of part (i) and re-solubilized by dialysis or diafiltration or ultrafiltration process to form a homogeneous injectable gel.

* * * * *